(12) United States Patent
Chaplin et al.

(10) Patent No.: US 11,419,934 B2
(45) Date of Patent: Aug. 23, 2022

(54) USE OF VDAS TO ENHANCE IMMUNOMODULATING THERAPIES AGAINST TUMORS

(71) Applicant: Oncotelic Therapeutics, Inc., Agoura Hills, CA (US)

(72) Inventors: David J. Chaplin, Watlington (GB); Kimberly Perkins, Belmont, CA (US)

(73) Assignee: Oncotelic Therapeutics, Inc., Agoura Hills, CA (US)

(*) Notice: Subject to any disclaimer, the term of this patent is extended or adjusted under 35 U.S.C. 154(b) by 0 days.

(21) Appl. No.: 15/753,882

(22) PCT Filed: Aug. 17, 2016

(86) PCT No.: PCT/US2016/047267
§ 371 (c)(1),
(2) Date: Feb. 20, 2018

(87) PCT Pub. No.: WO2017/031157
PCT Pub. Date: Feb. 23, 2017

(65) Prior Publication Data
US 2019/0008956 A1 Jan. 10, 2019

Related U.S. Application Data

(60) Provisional application No. 62/206,719, filed on Aug. 18, 2015.

(51) Int. Cl.
*A61K 39/395* (2006.01)
*A61K 31/661* (2006.01)
(Continued)

(52) U.S. Cl.
CPC ........ *A61K 39/3955* (2013.01); *A61K 31/661* (2013.01); *A61K 31/6615* (2013.01);
(Continued)

(58) Field of Classification Search
CPC .............. A61K 2300/00; A61K 31/661; A61K 31/6615; A61K 39/395; A61K 2039/505;
(Continued)

(56) References Cited

U.S. PATENT DOCUMENTS 4,659,701 A 4/1987 Wuest et al.
4,940,726 A 7/1990 Pettit et al.
(Continued)

FOREIGN PATENT DOCUMENTS

EP 0276051 A2 7/1988
EP 1262193 A1 12/2002
(Continued)

OTHER PUBLICATIONS

Arditti et al., Apoptotic killing of B-chronic lymphocytic leukemia tumor cells by allicin generated in situ using a rituximab-alliinase conjugate. Molecular Cancer Therapeutics; 4(2); pp. 325-331; Feb. 1, 2005.
(Continued)

*Primary Examiner* — Savitha M Rao
(74) *Attorney, Agent, or Firm* — Shay Glenn LLP (57) ABSTRACT

Methods for producing an anti-tumor effect in a subject suffering from a cancer or a tumor are disclosed. The methods comprise administering to the patient a Vascular Disrupting Agent (VDA) that a combretastatin agent and one or more antibodies selected from the group consisting of: a CTLA-4 antibody, a PD-1 antibody, a PD-L1 antibody, and a PD-L2 antibody in amounts effective therefor. Examples of combretastatin include CA1P, CA4P, and their corresponding salts and prodrugs. The combination of the VDA and one or more of the antibodies produced a synergistic anti-tumor effect.

5 Claims, 2 Drawing Sheets

(51) Int. Cl.
*A61K 31/6615* (2006.01)
*C07K 16/28* (2006.01)
*A61P 35/00* (2006.01)
*A61K 39/00* (2006.01)

(52) U.S. Cl.
CPC ............ *A61K 39/395* (2013.01); *A61P 35/00* (2018.01); *C07K 16/2818* (2013.01); *A61K 2039/505* (2013.01); *C07K 2317/76* (2013.01)

(58) Field of Classification Search
CPC . A61K 39/3955; A61P 35/00; C07K 16/2818; C07K 2317/07
See application file for complete search history.

(56) References Cited

U.S. PATENT DOCUMENTS

| | | |
|---|---|---|
| 4,996,237 A | 2/1991 | Pettit et al. |
| 5,231,112 A | 7/1993 | Janoff et al. |
| 5,409,953 A | 4/1995 | Pettit et al. |
| 5,430,062 A | 7/1995 | Cushman et al. |
| 5,525,632 A | 6/1996 | Ohsumi et al. |
| 5,561,122 A | 10/1996 | Pettit |
| 5,674,906 A | 10/1997 | Hatanaka et al. |
| 6,025,507 A | 2/2000 | Klar et al. |
| 6,150,407 A | 11/2000 | Tuse et al. |
| 6,169,104 B1 | 1/2001 | Tuse et al. |
| 6,201,001 B1 | 3/2001 | Wang et al. |
| 6,423,753 B1 | 7/2002 | Dougherty |
| 6,433,012 B1 | 8/2002 | Tuse et al. |
| 6,538,038 B1 | 3/2003 | Pero et al. |
| 6,593,374 B2 | 7/2003 | Pinney et al. |
| 6,670,344 B2 | 12/2003 | Venit et al. |
| 6,720,323 B2 | 4/2004 | Arnould |
| 6,723,858 B2 | 4/2004 | D'Amato et al. |
| 6,777,578 B2 | 8/2004 | Pettit et al. |
| 6,787,672 B2 | 9/2004 | Potter et al. |
| 6,794,384 B1 | 9/2004 | Potter et al. |
| 6,846,192 B2 | 1/2005 | Tien |
| 6,849,656 B1 | 2/2005 | Pinney et al. |
| 6,855,702 B2 | 2/2005 | Venit et al. |
| 6,919,324 B2 | 7/2005 | Chaplin et al. |
| 6,992,106 B2 | 1/2006 | Morinaga et al. |
| 7,018,987 B1 | 3/2006 | Pettit et al. |
| 7,030,123 B2 | 4/2006 | Arnould et al. |
| 7,037,906 B1 | 5/2006 | Lee |
| 7,087,627 B1 | 8/2006 | Davis |
| 7,105,501 B2 | 9/2006 | Davis |
| 7,105,695 B2 | 9/2006 | Pettit et al. |
| 7,125,906 B2 | 10/2006 | Arnould |
| 7,358,236 B1 | 4/2008 | Chaplin et al. |
| 8,198,302 B2 | 6/2012 | Chaplin et al. |
| 9,040,500 B2 | 5/2015 | Chaplin et al. |
| 2002/0035090 A1 | 3/2002 | Zeldis et al. |
| 2002/0119951 A1 | 8/2002 | Seyedi et al. |
| 2002/0183266 A1 | 12/2002 | Bissery |
| 2003/0220298 A1 | 11/2003 | Pettit et al. |
| 2004/0024696 A1 | 2/2004 | Alves |
| 2006/0166942 A1 | 7/2006 | Venit et al. |
| 2006/0172980 A1 | 8/2006 | Venit et al. |
| 2007/0149476 A1 | 6/2007 | Bissery |
| 2007/0270617 A1 | 11/2007 | Venit et al. |
| 2009/0192098 A1 | 7/2009 | Chaplin et al. |
| 2009/0264382 A1 | 10/2009 | Chaplin et al. |
| 2015/0132217 A1* | 5/2015 | Chang ............... A61K 38/21 424/1.11 |
| 2015/0140349 A1* | 5/2015 | Lee ................... C08J 3/075 428/478.2 |
| 2015/0141349 A1 | 5/2015 | Davis et al. |
| 2015/0246064 A1 | 9/2015 | Chaplin et al. |
| 2018/0161302 A1* | 6/2018 | Kremmidiotis ........ A61K 45/06 |

FOREIGN PATENT DOCUMENTS

| | | |
|---|---|---|
| WO | WO92/16486 A1 | 10/1992 |
| WO | WO99/34788 A1 | 7/1999 |
| WO | WO99/35150 A1 | 7/1999 |
| WO | WO99/48495 A1 | 9/1999 |
| WO | WO00/06556 A1 | 2/2000 |
| WO | WO00/35865 A2 | 6/2000 |
| WO | WO00/48590 A1 | 8/2000 |
| WO | WO00/48606 A1 | 8/2000 |
| WO | WO00/73264 A1 | 12/2000 |
| WO | WO01/12579 A2 | 2/2001 |
| WO | WO01/84929 A1 | 11/2001 |
| WO | WO02/22626 A1 | 3/2002 |
| WO | WO02/50007 A2 | 6/2002 |
| WO | WO02/056692 A1 | 7/2002 |
| WO | WO03/006743 A2 | 1/2003 |
| WO | WO03/035008 A2 | 5/2003 |
| WO | WO03/040077 A1 | 5/2003 |
| WO | WO2004/078126 A2 | 9/2004 |
| WO | WO2005/007635 A2 | 1/2005 |
| WO | WO2006/138427 A2 | 12/2006 |
| WO | WO2015/118030 A2 | 8/2015 |
| WO | WO2016/197204 A1 | 12/2016 |

OTHER PUBLICATIONS

Benezra et al.; Serial monitoring of human systemic and zenograft models of leukemia using a novel vascular disrupting agent; Leukemia; 26(8); pp. 1771-1778; Aug. 2012.

Berge et al.; Pharmaceutical salts; Journal of Pharmaceutical Sciences;66(1); pp. 1-19; Jan. 1, 1977.

Bishop et al., A randomized study of high-dose cytarabine in induction in acute myeloid leukemia; Blood; 87(5); pp. 1710-1717; Mar. 1, 1996.

Chaplin et al.; Anti-vascular approaches to solid tumour therapy: evaluation of combretastatin A4 phosphate; Anticancer Res.; 19(1A); pp. 189-196; Jan.-Feb. 1999.

Combreu et al., RPR112378 and RPR115781: Two Representatives of a New family of Microtubule Assembly Inhibitors; Molecular Pharmacology; 57(3); pp. 553-563; Mar. 1, 2000.

Dark et al.; Combretastatin A-4, an agent that displays potent and selective toxicity toward tumor vasculature; 57(10); pp. 1829-1834; May 15, 1997.

Fang et al., MZ3 induces apoptosis in human leukemia cells; Cancer Chemotherapy and Pharmacology; 59(3); pp. 397-405; Mar. 1, 2007.

Folkes et al., Oxidative Metabolism of Combretastatin A-1 Produces Quinone Intermediates with the Potential to Bind to Nucleophiles and to Enhance Oxidative Stress via Free Radicals; Chemical Research in Toxicology; 20(12); pp. 1885-1894; Dec. 20, 2007.

Gamrekelashvii et al.; Necotic tumor cell death in vivo impairs tumor-specific immune responses; J. Immunol.; 178(3); pp. 1573-1580; Feb. 1, 2007.

Hill et al.; Preclinical evaluation of the antitumour activity of the novel vascular targeting agent OXI 4503; 22(3); pp. 1453-1458; May-Jun. 2002.

Holwell et al.; Combretastatin A-1 phosphate a novel tubulin-binding agent with in vivo anti vascular effects in experimental tumours; Anticancer Res.; 22(2A); pp. 707-712; Mar.-Apr. 2002.

Kaffy et al., Synthesis and biological evaluation of vinylogous combretastatin A-4 derivatives; Organic and Biomolecular Chemistry; 3(14); pp. 2657-2660; Jul. 2005.

Lin et al., Functional activity of three distinct myeloperoxidase (MPO) promoters in human myeloid cells; Leukemia; 16(6); pp. 1143-1153; Jun. 2002.

Lin et al.; Antimitotic natural products combretastatin A-4 and combretastatin Aa-2: studies on the mechanism of their inhibition of the binding of colchicine to tubulin; Biochemistry; 28(17); pp. 6984-6991; Aug. 1, 1989.

Madlambayan et al.; Leukemia regression by vascular disruption and antiangiogenic therapy; Blood; 116(9); pp. 1539-1547; Sep. 2, 2010.

(56) References Cited

OTHER PUBLICATIONS

Nabha et al., Evaluation of combretastatin A-4 prodrug in a non-Hodgkin's lymphoma xenograft model: preclinical efficacy; Anticancer Drugs; 12(1); pp. 57-63; Jan. 1, 2001.

Nabha et al.; Combretastatin-A4 Prodrug Induces Mitotic Catastrophe in Chronic Lymphocytic Leukemia Cell Line Independent of Caspase Activation and Poly(ADP-ribose) Polymerase Cleavage; Clinical Cancer Research; 8(8); pp. 2735-2741; Aug. 1, 2002.

Nabha et al.; Effects of Combretastatin A-4 prodrug against a panel of malignant human B-lymphoid cell lines; Anticancer Drugs; 11(5); pp. 385-392; Jun. 1, 2000.

Niazi et al.; Leukemic dermal infiltrates at permanent indwelling central venous catheter insertion sites; Cancer; 68(10); pp. 2281-2283; Nov. 1991; (Abstract/Summary; 4pgs.); retrieved May 20, 2011 from the internet: http://www.readabstracts.com/Health/Leukemic-dermal-infiltrates-at-permanent-central-venous-catheter-insertion-sites.html; 4 pgs.

Oh et al.; Expression of functional markers in acute lymphoblastic leukemia; Leukemia Research; 27(10); pp. 903-908; Oct. 2003.

Patterson et al.; Phase 1 clinical and pharmacokinetic evaluation of the vascular-disrupting agent OXi4503 in patients with advanced solid tumors; Clinical Cancer Research; 18(5); pp. 1415-1425; Mar. 2012.

Petit et al., "The microtubule-targeting agent CA4P regresses leukemic xenografts by disrupting interaction with vascular cells and mitochondrial-dependent cell death." Blood; 111(4); pp. 1951-1961; Feb. 2008.

Pettit et al.; Antineoplastic agents 429, syntheses of the combretastatin A-1 and combretastatin B-1 prodrugs; Anti Cancer Drug Design; 15(3); pp. 203-216; Jun. 1, 2000.

Pettit et al.; Antineoplastic agents 460. Synthesis of combretastatin A-2 prodrugs; Anticancer Drug Design; 16(4-5); pp. 185-193; Aug.-Oct. 2001.

Pettit et al.; Antineoplastic agents, 122. Constituents of combretum caffrum; Journal of Natural Products; 50(3); pp. 386-391; May-Jun. 1987.

Pettit et al.; Antineoplastic agents. 291. Isolation and synthesis of combretastatins A-4, A-5, and A-6; J. Med. Chem.; Journal of Medicinal Chemistry; 38(10); pp. 1666-1672; May 1995.

Pettit et al.; Isolation and structure of combretastatin; Can. J. Chem.; 60(11); pp. 1374-1376; Jun. 1, 1982.

Pettit et al.; Synthesis of natural (-)- combretastatin; J. Org. Chem.; 50(18); pp. 3404-3406; Sep. 1985.

PETTIT; Antineoplastic agents 393. Synthesis of the trans-isomer of combretastatin A-4 prodrug; Anti-Cancer Drug Design; 13(8); 981-993; Dec. 1998.

Rice et al.; Support for a free radical mechanism for enhanced antitumor efficacy of the microtubule disruptor OXi4503; Microvasc Res.; 81(1); pp. 44-51; (Author Manuscript; 18 pgs.); Jan. 2011.

Sidney Kimmel Comprehensive Cancer Center; Clofarabine and cyclophosphamide in treating patients with relapsed or refractory acute leukemia, chronic myelogenous leukemia, or myeloproliferative disorders (clinical trial summary); U.S. Nat. Inst. of Health (ClinicalTrials.gov); NCT00293410; 4 pgs.; Feb. 2006.

Thomson et al.; Synthesis and biological properties of bioreductively targeted nitrothienyl prodrugs of combretastatin A-4; Molecular Cancer Therapeutics; 5(11); pp. 2886-2894; Nov. 1, 2006.

Vardiman; The World Health Organization (WHO) classification of tumors of the hematopoietic and lymphoid tissues: An overview with emphasis on the myeloid neoplasms; Chemico-Biological Interactions; 184(1-2); pp. 16-20; Mar. 2010.

Wikipedia; Hematopathology; 2 pgs.; retrieved from the internet: (http//en.wikipedia.org/wiki/Hematopathology) on Jul. 30, 2014.

Wood et al.; Induction of apoptosis by anti-cancer drugs with disparate modes of action: kinetics of cell death and changes in c-myc expression; British Journal of Cancer, 71(5); pp. 937-941; May 1995.

Kremmidiotis et al.; BNC105: a novel tubulin polymerization inhibitor that selectively disrupts tumor vasculature and displays single-agent antitumor efficacy; Molecular Caner Therapeutics; 9(6); pp. 1562-1573; Jun. 1, 2010.

Salmon et al.; Effect of the second-generation vascular disrupting agent OXi4503 on tumor vascularity; Clinical Cancer Research; 12(13); pp. 4090-4094; Jul. 1, 2006.

Flynn et al.; Discovery of 7-Hydroxy-6-methoxy-2-methyl-3-(3,4,5-trimethoxybenzoyl) benzo[b] furan (BNC105), a tubulin polymerization inhibitor with potent antiproliferative and tumor vascular disrupting properties; Journal of Medicinal Chemistry; 54(17); pp. 6014-6027; Sep. 2011.

Wu et al.; Mechanisms of tumor resistance to small-molecule vascular disrupting agents: Treatment and rationale of combination therapy; Journal of the Formosan Medical Association; 112(3); pp. 115-124; Mar. 2013.

* cited by examiner

USE OF VDAS TO ENHANCE IMMUNOMODULATING THERAPIES AGAINST TUMORS

CROSS REFERENCE TO RELATED APPLICATIONS

The present application claims priority under 35 U.S.C. 119 to U.S. provisional patent application Ser. No. 62/206,719 filed Aug. 18, 2015, titled "Use of VDAs to Enhance Immunomodulating Therapies Against Tumors", the disclosure of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present application relates generally to cancer treatments.

BACKGROUND

Due to the wide variety of cancers presently observed, numerous anticancer agents have been developed to destroy cancer within the body. These compounds are administered to cancer patients with the objective of destroying or otherwise inhibiting the growth of malignant cells while leaving normal, healthy cells undisturbed.

Anticancer agents have been classified based upon their mechanism of action. One promising new class of chemotherapeutic are referred to as a Vascular Disrupting Agents (VDAs) (or alternatively, Vascular Damaging Agents, Vascular Targeting Agents (VTAs) or Anti-vascular agents). The primary mechanism of action of VDAs is "vascular targeting", in which the neovasculature of solid tumors is selectively disrupted, resulting in a transient decrease or complete shutdown of tumor blood flow that results in secondary tumor cell death due to hypoxia, acidosis, and/or nutrient deprivation (Dark et al., Cancer Res., 57: 1829-34, (1997); Chaplin et al., Anticancer Res., 19: 189-96, (1999); Hill et al., Anticancer Res., 22(3):1453-8 (2002); Holwell et al., Anticancer Res., 22(2A):707-11, (2002). Vascular disrupting agents (VDAs) cause acute shutdown of the established tumor vasculature, which is followed by massive intratumoral hypoxia and necrosis. While VDAs have strong activity against a variety of tumors, a viable rim of tumor tissue typically surrounds a massive necrotic tumor center after treatment. Rapid tumor regrowth can resume from this residual viable rim, driven by an acute systemic mobilization of bone marrow derived circulating endothelial precursor cells (CEPs) which home to the viable tumor rim and stimulate revascularization.

Improved therapies for treating cancer, including therapies that prevent tumor revascularization and regrowth are desired.

SUMMARY OF THE DISCLOSURE

The present invention relates to methods for treating cancer. The methods can include producing an anti-tumor effect in a subject suffering from cancer or a tumor. The methods can include administering to the patient a Vascular Disrupting Agent (VDA) that is a combretastatin agent and one or more antibodies selected from the group consisting of: cytotoxic T-lymphocyte-associated protein 4 (CTLA-4) antibody, programmed cell death protein 1 (PD-1) antibody, programmed death-ligand 1 (PD-L1) antibody, and programmed death-ligand 2 (PD-L2) antibody in amounts effective therefor. The combination of the combretastatin agent and the antibodies can produce a synergistic effect against the cancer or tumor.

In general, in one embodiment, a method for producing an anti-tumor effect in a subject suffering from cancer or a tumor, the method including administering to the patient a Vascular Disrupting Agent (VDA) that is a combretastatin agent and one or more antibodies selected from the group consisting of: a CTLA-4 antibody, a PD-1 antibody, a PD-L1 antibody, and a PD-L2 antibody in amounts effective therefor.

In general, in one embodiment, a method for preventing tumor regrowth in a subject suffering from cancer or a tumor, the method including administering to the patient a Vascular Disrupting Agent (VDA) that is a combretastatin agent and one or more antibodies selected from the group consisting of: a CTLA-4 antibody, a PD-1 antibody, a PD-L1 antibody, and a PD-L2 antibody in amounts effective therefor.

In general, in one embodiment, a method for inhibiting tumor-associated angiogenesis in a subject that is treated with a Vascular Disrupting Agent (VDA) that is a combretastatin agent, the method including administering to the patient one or more antibodies selected from the group consisting of: a CTLA-4 antibody, a PD-1 antibody, a PD-L1 antibody, and a PD-L2 antibody in amounts effective therefor.

In general, in one embodiment, a method for the treatment of cancer, including: administering to a subject in need of a synergistic, therapeutically effective amount of (1) a Vascular Disrupting Agent that is a combretastatin agent; and (2) one or more antibodies selected from the group consisting of: a CTLA-4 antibody, a PD-1 antibody, a PD-L1 antibody, and a PD-L2 antibody.

This and other embodiments can include one or more of the following features. The method can include administering two or more antibodies selected from the group consisting of: a CTLA-4 antibody, a PD-1 antibody, a PD-L1 antibody, and a PD-L2 antibody. The method can include administering a CTLA-4 antibody, a PD-1 antibody, a PD-L1 antibody, and a PD-L2 antibody in a therapeutically effective amount. The combretastatin agent can be combretastatin A1 diphosphate (CA1P) or combretastatin A4 phosphate (CA4P). The CTLA-4 antibody, PD-1 antibody, PD-L1 antibody, and a PD-L2 antibody can be selected from the group consisting of: Tremelimumab, Ipilumab, Nivolumab, Pembrolizumab, Pidilizumab, MEDI4736, BMS 936559, MPDL328OA, and AMP-224. The compounds can be simultaneously or sequentially administered. The combretastatin agent can be administered prior to the antibody. The combretastatin agent can be administered more than about 12 hours prior to the antibody. Said cancer can be selected from the group consisting of: ovarian cancer, fallopian tube cancer, cervical cancer, breast cancer, lung cancer, melanoma, kidney, and primary cancer of the peritoneum. The tumor can be a solid tumor selected from the group consisting of: a melanoma, an ovarian tumor, a cervical tumor, a breast tumor, small cell lung tumor, a non-small cell lung tumor, a fallopian tube tumor, a primary tumor of the peritoneum, a glioblastoma multiforme, gliomas, astrocytomas, thyroid carcinoma, neuroendocrine tumors, soft tissue sarcomas, hepatocellular carcinoma, and gastrointestinal stromal tumors. Said cancer can be selected from the group consisting of: hematologic malignancies, acute leukemias, chronic leukemias, lymphomas, and myelomas. The tumor can have a diameter or length that can be greater than about 5 cm. The tumor can have a diameter or length that can be greater than about 7 cm. The tumor can have a diameter or length that can be greater than about 10 cm. The combretastatin agent can be a compound of Formula II:

(II)

or a pharmaceutically acceptable salt thereof, wherein $R^a$ can be H, phosphate, phosphate ester, phosphonate, phosphoramidate monoester, phosphoramidate diester, cyclic phosphoramidate, phosphordiamidate, cyclic phosphorodiamidate, phosphonamidate or amino acid acyl; and $R^b$ can be phosphate, phosphate ester, phosphonate, phosphoramidate monoester, phosphoramidate diester, cyclic phosphoramidate, phosphordiamidate, cyclic phosphorodiamidate, phosphonamidate or amino acid acyl. The combretastatin agent can be a compound of Formula IIb:

(IIb)

wherein $R^a$ can be H or $OP(O)(OR^3)OR^4$; and $OR^1$, $OR^2$, $OR^3$ and $OR^4$ can be each, independently, H, —O-QH$^+$ or —O— M$^+$, wherein M$^+$ can be a monovalent or divalent metal cation, and Q can be, independently: a) an amino acid containing at least two nitrogen atoms where one of the nitrogen atoms, together with a proton, can form a quaternary ammonium cation QH$^+$; or b) an organic amine containing at least one nitrogen atom which, together with a proton, can form a quaternary ammonium cation, QH$^+$. For Formula IIb, $R^3$ can be H or $OP(O)(OR^3)OR^4$, and $R^1$, $R^2$, $R^3$ and $R^4$ can be each, independently, an aliphatic organic amine, alkali metals, transition metal, heteroarylene, heterocyclyl, nucleoside, nucleotide, alkaloid, amino sugar, amino nitrile, or nitrogenous antibiotic. For Formula IIb, $R^1$, $R^2$, $R^3$ and $R^4$ can be each, independently, Na, TRIS, histidine, ethanolamine, diethanolamine, ethylenediamine, diethylamine, triethanolamine, glucamine, N-methylglucamine, ethylenediamine, 2-(4-imidazolyl)-ethylamine, choline, or hydrabamine. Formula II or Formula IIb can be represented by a compound of Formula III:

(III)

and pharmaceutically acceptable salts thereof.

In general, in one embodiment, a method of treating a tumor in a subject in need thereof by administering to the subject a pharmaceutical composition including combretastatin A1 diphosphate (CA1P) and one or more compound selected from the group consisting of: Tremelimumab, Ipilumab, Nivolumab, Pembrolizumab, Pidilizumab, MEDI4736, BMS 936559, MPDL328OA, and AMP-224.

In general, in one embodiment, a method of treating a tumor in a subject in need thereof by administering to the subject a pharmaceutical composition including combretastatin A4 phosphate (CA4P) and one or more compound selected from the group consisting of: Tremelimumab, Ipilumab, Nivolumab, Pembrolizumab, Pidilizumab, MEDI4736, BMS 936559, MPDL328OA, and AMP-224.

This and other embodiments can include one or more of the following features. The subject can be a human. The tumor can have a diameter or length that can be greater than about 5 cm. The tumor can have a diameter or length that can be greater than about 7 cm. The tumor can have a diameter or length that can be greater than about 10 cm.

In general, in one embodiment, a pharmaceutical composition for producing an anti-tumor effect in a subject suffering from cancer or a tumor, including a Vascular Disrupting Agent (VDA) including a combretastatin agent and one or more antibodies selected from the group consisting of: a CTLA-4 antibody, a PD-1 antibody, a PD-L1 antibody, and a PD-L2 antibody in amounts effective therefore in a pharmaceutical carrier.

This and other embodiments can include one or more of the following features. The CTLA-4 antibody, PD-1 antibody, PD-L1 antibody, and a PD-L2 antibody can be selected from the group consisting of: Tremelimumab, Ipilumab, Nivolumab, Pembrolizumab, Pidilizumab, MEDI4736, BMS 936559, MPDL328OA, and AMP-224. The composition can include two or more antibodies selected from the group consisting of: Tremelimumab, Ipilumab, Nivolumab, Pembrolizumab, Pidilizumab, MEDI4736, BMS 936559, MPDL328OA, and AMP-224. The VDA can be combretastatin A1 diphosphate (CA1P) or combretastatin A4 phosphate (CA4P). The combretastatin agent can be a compound of Formula II:

(II)

or a pharmaceutically acceptable salt thereof, wherein $R^a$ can be H, phosphate, phosphate ester, phosphonate, phosphoramidate monoester, phosphoramidate diester, cyclic phosphoramidate, phosphordiamidate, cyclic phosphorodiamidate, phosphonamidate or amino acid acyl; and $R^b$ can be phosphate, phosphate ester, phosphonate, phosphoramidate monoester, phosphoramidate diester, cyclic phosphoramidate, phosphordiamidate, cyclic phosphorodiamidate, phosphonamidate or amino acid acyl. The combretastatin agent can be a compound of Formula IIb:

wherein $R^a$ can be H or $OP(O)(OR^3)OR^4$; and $OR^1$, $OR^2$, $OR^3$ and $OR^4$ can each, independently, H, —O— $QH^+$ or —O— $M^+$, wherein $M^+$ can be a monovalent or divalent metal cation, and Q can be, independently: a) an amino acid containing at least two nitrogen atoms where one of the nitrogen atoms, together with a proton, can form a quaternary ammonium cation $QH^+$; or b) an organic amine containing at least one nitrogen atom which, together with a proton, can form a quaternary ammonium cation, $QH^+$. For Formula IIb, $R^3$ can be H or $OP(O)(OR^3)OR^4$, and $R^1$, $R^2$, $R^3$ and $R^4$ can each, independently, an aliphatic organic amine, alkali metals, transition metal, heteroarylene, heterocyclyl, nucleoside, nucleotide, alkaloid, amino sugar, amino nitrile, or nitrogenous antibiotic. For Formula IIb, $R^1$, $R^2$, $R^3$ and $R^4$ can each, independently, Na, TRIS, histidine, ethanolamine, diethanolamine, ethylenediamine, diethylamine, triethanolamine, glucamine, N-methylglucamine, ethylenediamine, 2-(4-imidazolyl)-ethylamine, choline, or hydrabamine. Formula II or IIb can be represented by a compound of Formula III:

and pharmaceutically acceptable salts thereof. The pharmaceutical composition can include CA1P and one or more compounds selected from the group consisting of: Tremelimumab, Ipilumab, Nivolumab, Pembrolizumab, Pidilizumab, MEDI4736, BMS 936559, MPDL3280OA, and AMP-224. The pharmaceutical composition can include CA4P and one or more compounds selected from the group consisting of: Tremelimumab, Ipilumab, Nivolumab, Pembrolizumab, Pidilizumab, MEDI4736, BMS 936559, MPDL3280OA, and AMP-224.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

The present application relates to the surprising and unexpected discovery of the synergistic combination of a VDA that is a combretastatin agent and one or more antibodies for CTLA-4, PD-1, PD-L1, and PD-L2. As disclosed herein the combination of a combretastatin agent and CTLA-4, PD-1, PD-L1, and/or PD-L2 antibodies produced a much greater response against cancer tumors than any of the compounds by themselves.

It is believed that the combination of necrotic cell death caused by the VDA in combination with the antibodies blocking one or more of the CTLA-4, PD-1, PD-L1, and PD-L2 receptors on the T-call can provide greatly improved immune system responses against the tumor. The improved immune system response against the cancer or tumor can be reflected in a variety of different ways. In some embodiments the treatment includes tumor regression. In some embodiments the treatment includes producing an anti-tumor effect in the subject suffering from the cancer or a tumor. In some embodiments the treatment includes preventing tumor regrowth in a subject suffering from the cancer or a tumor. In some embodiments the treatment includes inhibiting tumor-associated angiogenesis in the subject suffering from the cancer or tumor. In some embodiments treatment includes producing a synergistic effect against the tumor that is greater than the combined effects of the individual therapies administered to the patient. The synergistic anti-tumor therapies described herein can also allow for lower drug dosages that can minimize side effects while exhibiting good anti-tumor effects.

CTLA-4 and PD-1 receptors on T cells can down regulate T cell function. Studies have suggested that blocking CTLA-4 and PD-1 pathways can impact anti-tumor immune responses. Callahan et al. ("CTLA-4 and PD-1 pathway blockade: combinations in the clinic" Frontiers in Oncology; January 2015, volume 4, article 385, pages 1-6) studied checkpoint blocking antibodies that target regulatory molecules on T cells like CTLA-4 and PD-1. A number of CTLA-4, PD-1, and PD-L1 antibodies are currently being evaluated. It is believed that the combination of necrotic cell death (caused by the VDA) and immune system response modifications from CTLA-4, PD-1, and PD-L1 antibodies can increase anti-tumor effects. However, Gamrekelashvili et al. found that VDA ZD6126 indicated that this VDA may reduce T-cell mediated immune response ("Necrotic Tumor Cell Death in Vivo Impairs Tumor-Specific Immune Responses" J. Immunol. 2007; 178: 1573-1580). The present application unexpectedly found a synergistic combination with a combretastatin agent and CTLA-4, PD-1, and PD-L1 antibodies.

Cytotoxic T-lymphocyte-associated protein 4 (CTLA-4), which is also known as CD152 (cluster of differentiation 152), is a protein receptor that functions as an immune checkpoint that down regulates the immune system. CTLA-4 antibodies can be used to target CTLA-4 and provide a boost to the immune system during cancer treatments. Examples of CTLA-4 antibodies include Tremelimumab formerly known as ticilimumab/CP-675,206 (MedImmune/AstraZeneca) and Ipilumab (Bristol-Myers Squibb). Ipilumab has FDA approval for treatment of melanoma.

Programmed cell death protein 1 is also known as PD-1 and CD279 (cluster differentiation 279). PD-1 is a cell surface receptor that is expressed on T cells and pro-B cells. PD-1 can bind between two ligands, PD-L1 and PD-L2. PD-1 functions as an immune checkpoint. PD-1 antibodies can be used to target PD-1 to provide a boost to the immune system during cancer treatments. Examples of PD-1 antibodies that are approved for use include Nivolumab (Opdivo, BMS-936558, Bristol-Myers Squibb) and Pembrolizumab (Keytruda, MK-3475, Merck). Other examples of PD-1 antibodies that are in early stage development include Pidilizumab (CT-011, Cure Tech).

The PD-L1 and PD-L2 ligands can also be targeted with antibodies. Programmed death-ligand 1 (PD-L1), also known as CD279 (cluster differentiation 279), is a transmembrane protein that can bind to PD-1. Examples of PD-L1 antibodies in clinical development included MEDI4736 (Medimmune/AstraZeneca), BMS 936559 (MDX-1105, Bristol-Myers Squibb), and MPDL328OA (Roche). Examples of PD-L2 antibodies in clinical development include AMP-224 (Medimmune).

In some embodiments other checkpoint inhibitors, besides the CTLA-4, PD-1, PD-L1, and PD-L2 antibodies can be used in combination with the combretastatin agents described herein. Examples of other checkpoint inhibitors include IMP321 (Immutep) and TRX518 (GITR, Inc). IMP321 (Immutep) is a soluble lymphocyte activation gene-3 immunoglobulin fusion protein and major histocompatibility complex class II agonist. TRX518 (GITR, Inc) is a monoclonal antibody against glucocorticoid-inducted tumor necrosis factor receptor-related gene.

The treatment methods disclosed herein can include one or more CTLA-4, PD-1, PD-L1, and PD-L2 antibodies and other checkpoint inhibitors. In some embodiments one antibody can be provided to the patient selected from the group consisting of: CTLA-4, PD-1, PD-L1, and PD-L2 antibodies. In some embodiments two antibodies can be provided to the patient selected from the group consisting of: CTLA-4, PD-1, PD-L1, and PD-L2 antibodies. In some embodiments all three CTLA-4, PD-1, PD-L1, and PD-L2 antibodies can be provided to the patient. In some embodiments multiple different CTLA-4 antibodies can be provided to the patient. In some embodiments multiple different PD-1 antibodies can be provided to the patient. In some embodiments multiple different PD-L1 antibodies can be provided to the patient. In some embodiments multiple different PD-L2 antibodies can be provided to the patient. In some embodiments multiple different checkpoint inhibitors can be provided to the patient. In some embodiments the checkpoint inhibitors are used in combination with one or more of the other antibodies disclosed herein. In some embodiments the checkpoint inhibitors are used with the combretastatin agent alone without the other antibodies disclosed herein.

A variety of combretastatin agents can be used with the CTLA-4, PD-1, PD-L1, and PD-L2 antibodies and checkpoint inhibitors described herein. A number of combretastatin agents are described herein. In some embodiments the combretastatin agent is combretastatin A1 diphosphate (CA1P). In some embodiments the combretastatin agent is combretastatin A4 phosphate (CA4P).

The treatments disclosed herein can be used to treat a variety of different tumors and cancers as discussed in greater detail below. In some embodiments the cancer is selected from the group consisting of: ovarian cancer, fallopian tube cancer, cervical cancer, breast cancer, lung cancer, melanoma, kidney, and primary cancer of the peritoneum. In some embodiments the tumor is a solid tumor selected from the group consisting of: a melanoma, an ovarian tumor, a cervical tumor, a breast tumor, small cell lung tumor, a non-small cell lung tumor, a fallopian tube tumor, a primary tumor of the peritoneum, a glioblastoma multiforme, gliomas, astrocytomas, thyroid carcinoma, neuroendocrine tumors, soft tissue sarcomas, hepatocellular carcinoma, and gastrointestinal stromal tumors. In some embodiments the cancer is selected from the group consisting of: hematologic malignancies, acute leukemias, chronic leukemias, lymphomas, and myelomas.

As used herein, the term "combretastatin" or "combretastatin compound" denotes at least one of the combretastatin family of compounds, derivatives or analogs thereof, their prodrugs (preferably phosphate prodrugs) and derivatives thereof, and salts of these compounds. Combretastatins include those anti-cancer compounds isolated from the South African tree *Combretum caffrum*, including without limitation, Combretastatins A-1, A-2, A-3, A-4, B-1, B-2, B-3, B-4, D-1, and D-2, and various prodrugs thereof, exemplified by Combretastatin A-4 phosphate (CA4P) compounds, Combretastatin A-1 diphosphate (CA1dP) compounds and salts thereof (see for example Pettit el al, *Can. J. Chem.*, (1982); Pettit et al., *J. Org. Chem.*, 1985; Pettit et al., *J. Nat. Prod.*, 1987; Lin et al., *Biochemistry*, (1989); Pettit et al., *J. Med. Chem.*, 1995; Pettit et al., *Anticancer Drug Design*, (2000); Pettit et al., *Anticancer Drug Design*, 16(4-5): 185-93 (2001)).

As used herein, the term combretastatin A-4 phosphate ("CA4P") denotes as least one of combretastatin A-4 phosphate prodrugs, derivatives thereof, and salts of these compounds. As used herein, the term combretastatin A-1 diphosphate ("CA1P") compound denotes as least one of combretastatin A-1 diphosphate prodrugs (e.g., CA1P), derivatives thereof, and salts of these compounds.

In a some embodiments the combretastatin agent is a compound of Formula II:

(II)

or a pharmaceutically acceptable salt thereof wherein $R^a$ is H, phosphate, phosphate ester, phosphonate, phosphoramidate monoester, phosphoramidate diester, cyclic phosphoramidate, phosphordiamidate, cyclic phosphorodiamidate, phosphonamidate or amino acid acyl; and $R^b$ is phosphate, phosphate ester, phosphonate, phosphoramidate monoester, phosphoramidate diester, cyclic phosphoramidate, phosphordiamidate, cyclic phosphorodiamidate, phosphonamidate or amino acid acyl.

In a preferred embodiment $R^a$ is a phosphate of formula:

and $R^b$ is a phosphate of formula:

wherein $OR^1$, $OR^2$, $OR^3$ and $OR^4$ are each, independently, H, —O-QH+ or —O-M+, wherein M+ is a monovalent or divalent metal cation, and Q is, independently:

a) an amino acid containing at least two nitrogen atoms where one of the nitrogen atoms, together with a proton, forms a quaternary ammonium cation QH+; or b) an organic amine containing at least one nitrogen atom which, together with a proton, forms a quaternary ammonium cation, QH+.

In a particular embodiment, the combretastatin agent is a compound of the Formula IIb:

wherein
$R^a$ is H or $OP(O)(OR^3)OR^4$; and
$OR^1$, $OR^2$, $OR^3$ and $OR^4$ are each, independently, H, —O-QH+ or —O-M+, wherein M+ is a monovalent or divalent metal cation, and Q is, independently:

a) an amino acid containing at least two nitrogen atoms where one of the nitrogen atoms, together with a proton, forms a quaternary ammonium cation QH+; or b) an organic amine containing at least one nitrogen atom which, together with a proton, forms a quaternary ammonium cation, QH+.

In one embodiment of Formula IIb, $R^a$ is H, one of $OR^1$ and $OR^2$ is hydroxyl, and the other is —O-QH+ where Q is L-histidine. In another embodiment of Formula IIb, $R^a$ is H, one of $OR^1$ and $OR^2$ is hydroxyl and the other is —O-QH+ and Q is tris(hydroxymethyl)amino methane ("TRIS").

In another embodiment of Formula IIb, $R^a$ is H or OP(O)$(OR^3)OR^4$, and $R^1$, $R^2$, $R^3$ and $R^4$ are each, independently, an aliphatic organic amine, alkali metals, transition metals, heteroarylene, heterocyclyl, nucleoside, nucleotide, alkaloid, amino sugar, amino nitrile, or nitrogenous antibiotic.

In another embodiment of Formula IIb, $R^1$, $R^2$, $R^3$ and $R^4$ are each, independently, Na, TRIS, histidine, ethanolamine, diethanolamine, ethylenediamine, diethylamine, triethanolamine, glucamine, N-methylglucamine, ethylenediamine, 2-(4-imidazolyl)-ethylamine, choline, or hydrabamine.

In another embodiment, Formula IIb is represented by a compound of Formula III:

wherein $OR^1$, $OR^2$, $OR^3$ and $OR^4$ are each, independently, H, —O-QH+ or —O-M+, wherein M+ is a monovalent or divalent metal cation, and Q is, independently:

a) an amino acid containing at least two nitrogen atoms where one of the nitrogen atoms, together with a proton, forms a quaternary ammonium cation QH+; or b) an organic containing at least one nitrogen atom which, together with a proton, forms a quaternary ammonium cation, QH+.

In one embodiment of Formula III, at least one of $OR^1$, $OR^2$, $OR^3$ and $OR^4$ is hydroxyl, and at least one of $OR^1$, $OR^2$, $OR^3$ and $OR^4$ is —O-QH+, where Q is L-histidine. In another embodiment of Formula III, at least one of $OR^1$, $OR^2$, $OR^3$ and $OR^4$ is hydroxyl, and at least one of $OR^1$, $OR^2$, $OR^3$ and $OR^4$ is TRIS.

The phrase "combination therapy" (or "co-therapy") embraces the administration of a CTLA-4, PD-1, PD-L1, and/or PD-L2 antibody and a VDA such as a combretastatin agent, as part of a specific treatment regimen intended to provide a beneficial effect from the co-action of the antibody and the VDA.

Administration of the CTLA-4, PD-1, PD-L1, and/or PD-L2 antibody and the VDA in combination typically is carried out over a defined time period (usually minutes, hours, days or weeks depending upon the combination selected). "Combination therapy" generally is not intended to encompass the administration of a CTLA-4, PD-1, PD-L1, PD-L2 antibody and VDA as part of separate monotherapy regimens that incidentally and arbitrarily result in the combinations described herein. "Combination therapy" is intended to embrace administration of a CTLA-4, PD-1, PD-L1, and/or PD-L2 antibody and VDA in a sequential manner, that is, wherein the CTLA-4, PD-1, PD-L1, and/or PD-L2 antibody and the VDA are administered at different times, as well as administration of the CTLA-4, PD-1, PD-L1, and/or PD-L2 antibody and VDA in a substantially simultaneous manner. Substantially simultaneous administration can be accomplished, for example, by administering to the subject concurrently a single dosage having a fixed ratio of each therapeutic agent or in multiple, single dosage for each therapeutic agent. Sequential or substantially simultaneous administration of each therapeutic agent can be effected by any appropriate route including, but not limited to, oral routes, intravenous routes, intramuscular routes, and direct absorption through mucous membrane tissues. The therapeutic agents, if more than one, can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the CTLA-4, PD-1, PD-L1, and/or PD-L2 antibody and VDA are administered is not narrowly critical although the CTLA-4, PD-1, PD-L1, and/or PD-L2 antibody typically will follow the administration of the combretastatin agent. "Combination therapy" also can embrace the administration of the CTLA-4, PD-1, PD-L1 antibody and VDA as described above in further combination with other biologically active ingredients and non-drug therapies (such as, but not limited to, surgery).

The combretastatin agent can be administered simultaneously or sequentially with the CTLA-4, PD-1, PD-L1, and/or PD-L2 antibodies. In some cases the combretastatin agent can be administered prior to the CTLA-4, PD-1, PD-L1, and/or PD-L2 antibodies. For example, the combretastatin agent can be administered about 12 or more hours prior to the CTLA-4, PD-1, PD-L1, and/or PD-L2 antibodies. In some cases the combretastatin agent can be administered about 24 or more hours prior to the CTLA-4, PD-1, PD-L1, and/or PD-L2 antibodies.

The dosing schedule for the antibodies and VDA can be daily, every other day, multiple times per week, or as otherwise recommended. The agents can be administered for multiple weeks. In some embodiments the antibodies and VDA can be administered twice weekly for two or more consecutive weeks.

In some embodiments any of the compounds and combinations disclosed herein can be formulated into pharmaceutical compositions for administration to the subject.

In some embodiments any of the combination therapies described herein can be combined with other therapies: radiation therapy, surgery, chemotherapy, etc.

A suitable dose per day for each of the compounds, i.e., CTLA-4, PD-1, PD-L1, and PD-L2 antibody, and a VDA (e.g. a combretastatin), can be, individually, in the range of from about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 µg to about 3,500 mg, about 5 µg to about 3,000 mg, about 10 µg to about 2,600 mg, about 20 µg to about 2,575 mg, about 30 µg to about 2,550 mg, about 40 µg to about 2,500 mg, about 50 µg to about 2,475 mg, about 100 µg to about 2,450 mg, about 200 µg to about 2,425 mg, about 300 µg to about 2,000, about 400 µg to about 1,175 mg, about 500 µg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg.

Other suitable doses for the compounds include, for example, 0.1 mg/kg to about 100 mg/kg; from about 1 mg/kg to about 100 mg/kg; from about 5 mg/kg to about 50 mg/kg; from about 10 to about 25 mg/kg; about 10 mg/kg; about 15 mg/kg; about 20 mg/kg; about 25 mg/kg; about 30 mg/kg; about 40 mg/kg; about 50 mg/kg; about 60 mg/kg; about 70 mg/kg; about 80 mg/kg; about 90 mg/kg; and about 100 mg/kg. In some embodiments, the VDA (e.g., a combretastatin agent such as CA4P) is administered at a dose ranging from between 20 mg/m$^2$ and 80 mg/m$^2$. The methods disclosed herein can include providing the manufacturer's recommended dosage level for one or more of the antibodies selected from the group consisting of: Tremelimumab, Ipilumab, Nivolumab, Pembrolizumab, Pidilizumab, MEDI4736, BMS 936559, MPDL328OA, and AMP-224.

In some embodiments the dosage levels for the combretastatin agent and the antibody can be provided in an effective amount. As used herein, the term "effective amount" of a compound or pharmaceutical composition refers to an amount sufficient to provide the desired anti-cancer effect or anti-tumor effect in an animal, preferably a human, suffering from cancer. Desired anti-tumor effects include, without limitation, the modulation of tumor growth (e.g. tumor growth delay), tumor size, or metastasis, the reduction of toxicity and side effects associated with a particular anti-cancer agent, the enhancement of tumor necrosis or hypoxia, the reduction of tumor angiogenesis, the reduction of tumor re-growth, reduced tumor retention of CEPs and other pro-angiogenic cells, the amelioration or minimization of the clinical impairment or symptoms of cancer, extending the survival of the subject beyond that which would otherwise be expected in the absence of such treatment, and the prevention of tumor growth in an animal lacking any tumor formation prior to administration, i.e., prophylactic administration.

As used herein, the terms "modulate", "modulating" or "modulation" refer to changing the rate at which a particular process occurs, inhibiting a particular process, reversing a particular process, and/or preventing the initiation of a particular process. Accordingly, if the particular process is tumor growth or metastasis, the term "modulation" includes, without limitation, decreasing the rate at which tumor growth and/or metastasis occurs; inhibiting tumor growth and/or metastasis, including tumor re-growth following treatment with an anticancer agent; reversing tumor growth and/or metastasis (including tumor shrinkage and/or eradication) and/or preventing tumor growth and/or metastasis.

A variety of different cancers and diseases can be treating using the combination therapies described herein. As used herein, the terms "tumor", "tumor growth" or "tumor tissue" can be used interchangeably, and refer to an abnormal growth of tissue resulting from uncontrolled progressive multiplication of cells and serving no physiological function. The term "subject" is intended to include mammals suffering from or afflicted with a tumor. Exemplary subjects include humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from a cancer.

The combination therapies described herein can be particularly effective for treating larger tumor sizes. Larger tumor sizes can have greater amounts of vasculature relative to smaller tumors. The vascular disrupting agents described herein, such as CA1P and CA4P, can provide an improved response against larger tumor sizes by disrupting the increased vasculature present in larger tumors. The improved vascular disruption of the larger tumor in combination with the antibody treatments described herein can provide a synergistic effect to boost the immune therapy response against the tumor to more effectively treat the targeted tumor. The tumor size can be expressed as a maximum length or maximum diameter for a dominant dimension of the tumor. In some embodiments the combination therapies described herein are provided to a patient with a tumor having a maximum length or diameter of greater than about 5 cm. In some embodiments the combination therapies described herein are provided to a patient with a tumor having a maximum length or diameter of greater than about 7 cm. In some embodiments the combination therapies described herein are provided to a patient with a tumor having a maximum length or diameter of greater than about 10 cm. For example, lung cancer tumors can be considered large tumors (non-small tumors) when the tumor has a diameter or length that is greater than about 5 cm. In another example, ovarian cancer tumors can be considered large tumors (non-small tumors) when the tumor has a diameter or length that is greater than about 5 cm.

In some embodiments, the methods disclosed herein are used to treat solid tumors. As is well-known in the art, solid tumors are quite distinct from non-solid tumors, such as those found in hematopoietic-related cancers. A solid tumor can be malignant, e.g. tending to metastasize and being life threatening, or benign. Examples of solid tumors that can be treated or prevented according to the methods described herein include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, gastric cancer, pancreatic cancer, breast cancer, ovarian cancer, fallopian tube cancer, primary carcinoma of the peritoneum, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, liver metastases, bile duct carcinoma, choriocarcinoma, seminoma, embryonal carcinoma, thyroid carcinoma such as anaplastic thyroid cancer, Wilms' tumor, cervical cancer, testicular tumor, lung carcinoma such as small cell lung carcinoma and non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In other embodiments, tumors comprising dysproliferative changes (such as metaplasias and dysplasias) can be treated or prevented with a pharmaceutical composition or the methods described herein in epithelial tissues such as those in the cervix, esophagus, and lung. Thus, the present disclosure provides for treatment of conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W.B. Saunders Co., Philadelphia, pp. 68 to 79). Hyperplasia is a form of controlled cell proliferation involving an increase in cell number in a tissue or organ, without significant alteration in structure or function. For example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder. For a review of such disorders, see Fishman et al., 1985, Medicine, 2d Ed., J. B. Lippincott Co., Philadelphia.

Other examples of tumors that are benign and can be treated or prevented in accordance with the methods described herein include arteriovenous (AV) malformations, particularly in intracranial sites and myelomas.

U.S. Pat. No. 9,040,500 discloses methods for treating hematopoietic neoplasms including the use of a combretastatin compound. The methods described herein for administering a combretastatin agent in combination with an antibody for CTLA-4, PD-1, and/or PD-L1 can be used to treat hematopoietic neoplasms as described in U.S. Pat. No. 9,040,500. Accordingly, one aspect of the present disclosure provides a method of treating a hematopoietic neoplasm, the method comprising administering, to a mammal suffering from a hematopoietic neoplasm, a therapeutically effective amount of a combretastatin compound and one or more of the antibodies for CTLA-4, PD-1, and/or PD-L1.

As is well-known in the art, solid tumors are quite distinct from non-solid tumors, such as those found in hematopoietic-related cancers. Examples of non-solid tumors include leukemias, such as myeloid leukemias and lymphoid leukemias, myelomas, and lymphomas. In some implementations, the non-solid tumor is a hematopoietic neoplasm, which is aberrant growth of cells of the hematopoietic system. Hematopoietic malignancies can have their origins in pluripotent stem cells, multipotent progenitor cells, oligopotent committed progenitor cells, precursor cells, and terminally differentiated cells involved in hematopoiesis. Some hematological malignancies are believed to arise from hematopoietic stem cells, which have the ability for self renewal. For instance, cells capable of developing specific subtypes of acute myeloid leukemia (AML) upon transplantation display the cell surface markers of hematopoietic stem cells, implicating hematopoietic stem cells as the source of leukemic cells. Although hematopoietic neoplasms often originate from stem cells, committed progenitor cells or more terminally differentiated cells of a developmental lineage can also be the source of some leukemias. For example, forced expression of the fusion protein Bcr/Abl (associated with chronic myelogenous leukemia) in common myeloid progenitor or granulocyte/macrophage progenitor cells produces a leukemic-like condition.

Hematopoietic neoplasms differ from solid tumors in being capable of circulating and having access to various organs through interaction with activated vascular cells. Indeed, some hematopoietic neoplastic cells may adhere to vascular cells, establishing perivascular infiltrates, and as such may be endowed with a unique mechanism of resistance to chemotherapy. Both circulating and vascular-adherent hematopoietic neoplasms require cytoskeletal stability to maintain mitochondrial and cellular function and avoid cell death.

In some implementations, the hematopoietic neoplasm treated is a lymphoid neoplasm, where the abnormal cells are derived from and/or display the characteristic phenotype of cells of the lymphoid lineage. Lymphoid neoplasms can be subdivided into B-cell neoplasms, T and NK-cell neoplasms, and Hodgkin's lymphoma. B-cell neoplasms can be further subdivided into precursor B-cell neoplasm and mature/peripheral B-cell neoplasm. Exemplary B-cell neoplasms are precursor B-lymphoblastic leukemia/lymphoma (precursor B-cell acute lymphoblastic leukemia) while exemplary mature/peripheral B-cell neoplasms are B-cell chronic lymphocytic leukemia/small lymphocytic lymphoma, B-cell prolymphocytic leukemia, lymphoplamacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma, and Burkitt's lymphoma/Burkitt cell leukemia. T-cell and NK-cell neoplasms are further subdivided into precursor T-cell neoplasm and mature (peripheral) T-cell neoplasms. Exemplary precursor T-cell neoplasm is precursor T-lymphoblastic lymphoma/leukemia (precursor T-cell acute lymphoblastic leukemia) while exemplary mature (peripheral) T-cell neoplasms are T-cell prolymphocytic leukemia T-cell granular lymphocytic leukemia, aggressive NK-cell leukemia, adult T-cell lymphoma/leukemia (HTLV-1), extranodal NK/T-cell lymphoma, nasal type, enteropathy-type T-cell lymphoma, hepatosplenic gamma-delta T-cell lymphoma, subcutaneous panniculitis-like T-cell lymphoma, Mycosis fungoides/Sezary syndrome, Anaplastic large-cell lymphoma, T/null cell, primary cutaneous type, Peripheral T-cell lymphoma, not otherwise characterized, Angioimmunoblastic T-cell lymphoma, Anaplastic large-cell lymphoma, T/null cell, primary systemic type. The third member of lymphoid neoplasms is Hodgkin's lymphoma, also referred to as Hodgkin's disease. Exemplary diagnosis of this class that can be treated with the compounds include, among others, nodular lymphocyte-predominant Hodgkin's lymphoma, and various classical forms of Hodgkin's disease, exemplary members of which are Nodular sclerosis Hodgkin's lymphoma (grades 1 and 2), Lymphocyte-rich classical Hodgkin's lymphoma, Mixed cellularity Hodgkin's lymphoma, and Lymphocyte depletion Hodgkin's lymphoma. In various implementations, any of the lymphoid neoplasms can be treated with the combretastatin compounds and antibodies as described herein.

In some implementations, the hematopoietic neoplasm treated is a myeloid neoplasm. This group comprises a large class of cell proliferative disorders involving or displaying the characteristic phenotype of the cells of the myeloid lineage. Myeloid neoplasms can be subdivided into myeloproliferative diseases, myelodysplastic/myeloproliferative diseases, myelodysplastic syndromes, and acute myeloid leukemias. Exemplary myeloproliferative diseases are chronic myelogenous leukemia (e.g., Philadelphia chromosome positive (t(9;22)(qq34;q11)), chronic neutrophilic leukemia, chronic eosinophilic leukemia/hypereosinophilic syndrome, chronic idiopathic myelofibrosis, polycythemia vera, and essential thrombocythemia. Exemplary myelodysplastic/myeloproliferative diseases are chronic myelomonocytic leukemia, atypical chronic myelogenous leukemia, and juvenile myelomonocytic leukemia. Exemplary myelodysplastic syndromes are refractory anemia, with ringed sideroblasts and without ringed sideroblasts, refractory cytopenia (myelodysplastic syndrome) with multilineage dysplasia, refractory anemia (myelodysplastic syndrome) with excess blasts, 5q-syndrome, and myelodysplastic syndrome. In various implementations, any of the myeloid neoplasms can be treated with the combretastatin compounds and antibodies described herein.

In some implementations, the combination therapies described herein, can be used to treat acute myeloid leukemias (AML), which represent a large class of myeloid neoplasms having its own subdivision of disorders. These subdivisions include, among others, AMLs with recurrent cytogenetic translocations, AML with multilineage dysplasia, and other AML not otherwise categorized. Exemplary AMLs with recurrent cytogenetic translocations include, among others, AML with t(8;21)(q22;q22), AML1(CBF-alpha)/ETO, Acute promyelocytic leukemia (AML with t(15;17)(q22;q11-12) and variants, PML/RAR-alpha), AML with abnormal bone marrow eosinophils (inv(16)(p13q22) or t(16;16)(p13;q11), CBFb/MYH11X), and AML with 11q23 (MLL) abnormalities. Exemplary AML with multilineage dysplasia are those that are associated with or without prior myelodysplastic syndrome. Other acute myeloid leukemias not classified within any definable group include, AML minimally differentiated, AML without maturation, AML with maturation, acute myelomonocytic leukemia, acute monocytic leukemia, acute erythroid leukemia, acute megakaryocytic leukemia, acute basophilic leukemia, and acute panmyelosis with myelofibrosis.

The combination therapy methods disclosed herein can also be used to treat carcinoid syndrome and neuroendocrine tumors. U.S. 2015/0141349 discloses using combretastatin compounds to treat carcinoid syndrome and neuroendocrine tumors, the disclosure of which is incorporated by reference herein in its entirety.

"Neuroendocrine tumors" refers to a cell proliferative disorder arising from secretary cells of the endocrine and nervous system, and develop from different endocrine glands (such as the pituitary, the parathyroid or the neuroendocrine adrenal glands), from endocrine islets (for example in the pancreas) or from endocrine cells dispersed between exocrine cells throughout the digestive and respiratory tracts Carcinoid syndrome is rare and is caused by carcinoid tumors—small, malignant or benign tumors that most commonly arise in the submucosa of the gastrointestinal tract. Carcinoid syndrome is the set of symptoms that may occur in patients who have carcinoid tumors. The syndrome occurs when carcinoid tumors overproduce substances, such as serotonin and chromogranin A, that normally circulate throughout the body. The serotonin produced by the carcinoid tumor is further metabolized to the most important serotonin metabolite, 5-hydroxyindoleacetic acid (5-HIAA).

This overproduction of serotonin and other hormones causes the symptoms of carcinoid syndrome which includes episodic flushing, diarrhea, wheezing, and potentially, the eventual development of carcinoid heart disease. Carcinoid tumors often do not produce noticeable symptoms until they spread to the liver. This is because most of the circulation from the gastrointestinal tract must pass through the liver before it reaches the rest of the body. The liver metabolizes most of the excess serotonin and other substances produced by the carcinoid tumors, preventing them from reaching tissues where they can cause symptoms. When carcinoid tumors metastasize to the liver, the substances they overproduce can more easily reach the bloodstream, and reach tissues where they can cause symptoms. Carcinoid patients may present with one or more of the individual symptoms of carcinoid syndrome. Certain implementations of the methods described herein are directed towards treatment of a mammal having one or more symptoms associated with carcinoid syndrome.

As used herein, the term "treating" carcinoid syndrome, or other symptoms associated with a hormone-producing neuroendocrine tumor, is intended to mean inhibiting production of a tumor-generated hormone, decreasing levels of tumor-induced hormone and causing the regression and palliation of carcinoid syndrome, i.e., reducing the number of flushing or diarrheal events and/or increase quality of life. Other desired effects include, without limitation, decreases in abdominal pain, heart disease, wheezing, bloating, or sweating, and extending the survival of the subject beyond that which would otherwise be expected in the absence of such treatment.

Accordingly, some embodiments provide a method of treating carcinoid syndrome, the method comprising administering, to a mammal suffering from one or more symptoms of carcinoid syndrome, a therapeutically effective amount of a vascular disrupting agent that is a combretastatin agent along with one or more antibodies for CTLA-4, PD-1, PD-L1, and PD-L2.

Diseases which can be treated in accordance with the methods described herein include, but are not limited: Accelerated Phase Chronic Myelogenous Leukemia; Acute Erythroid Leukemia; Acute Lymphoblastic Leukemia; Acute Lymphoblastic Leukemia in Remission; Acute Lymphocytic Leukemia; Acute Monoblastic and Acute Monocytic Leukemia; Acute Myelogenous Leukemia; Acute Myeloid Leukemia; Adenocarcinoma; Adenocarcinoma of the Colon; Adenocarcinoma of the Esophagus; Adenocarcinoma of the Lung; Adenocarcinoma of the Pancreas; Adenocarcinoma of the Prostate; Adenocarcinoma of the Rectum; Adenocarcinoma of the Stomach; Adenoid Cystic Carcinoma of the Head and Neck; Adenosquamous Cell Lung Cancer; Adult Giant Cell Glioblastoma; Advanced Adult Primary Liver Cancer; Advanced Gastrointestinal Stromal Tumor; Advanced Non-Nasopharyngeal Head and Neck Carcinoma; Advanced NSCLC; Advanced Solid Tumors; Agnogenic Myeloid; Metaplasia; Anaplastic Astrocytoma; Anaplastic Oligodendroglioma; Anaplastic Thyroid Cancer; Astrocytoma; Atypical Chronic Myelogenous Leukemia; B-Cell Adult Acute Lymphoblastic Leukemia; Bladder Cancer; Blastic Phase Chronic Myelogenous Leukemia; Bone Metastases; Brain Tumor; Breast Cancer; Breast Cancer in Situ; Breast Neoplasms; Brenner Tumor; Bronchoalveolar Cell Lung Cancer; Cancer of the Fallopian Tube; Carcinoma, Squamous Cell; Central Nervous System Cancer; Cervix Neoplasms; Childhood Acute Lymphoblastic Leukemia; Childhood Acute Lymphoblastic Leukemia in Remission; Childhood Brain Tumor; Childhood Central Nervous System Germ Cell Tumor; Childhood Cerebellar Astrocytoma; Childhood Chronic Myelogenous Leukemia; Childhood Ependymoma; Childhood Malignant Germ Cell Tumor; Childhood Oligodendroglioma; Childhood Soft Tissue Sarcoma; Chordoma; Chronic Eosinophilic Leukemia (CEL); Chronic Idiopathic Myelofibrosis; Chronic Myelogenous Leukemia; Chronic Myeloid Leukemia; Chronic Myelomonocytic Leukemia; Chronic Phase Chronic Myelogenous Leukemia; Colon Cancer; Colorectal Cancer; Congenital Fibrosarcoma; Dermatofibrosarcoma; Dermatofibrosarcoma Protuberans (DFSP); Desmoid Tumor; Endometrial Adenocarcinoma; Endometrial Adenosquamous Cell; Eosinophilia; Esophageal Cancer; Epidemic Kaposi's Sarcoma; Epithelial Mesothelioma; Esophageal Cancer; Esophagogastric Cancer; Essential Thrombocythemia; Ewing's Family of Tumors; Extensive Stage Small Cell Lung Cancer; Extrahepatic Bile Duct Cancer; Fallopian Tube Cancer; Familiar Hypereosinophilia; Fibrosarcoma; Follicular Thyroid Cancer; Gallbladder Cancer; Gastric Adenocarcinoma; Gastric Cancer; Gastroinstestinal Cancer; Gastrinoma; Gastrointestinal Carcinoid; Gastrointestinal Neoplasm; Gastrointestinal Stromal Tumor; Giant Cell Glioblastoma; Glioblastoma; Glioma; Glioblastoma Multiforme; Gliosarcoma; Grade I Meningioma; Grade II Meningioma; Grade III Meningioma; Head and Neck Cancer; Head and Neck Neoplasms; Hematopoietic and Lymphoid Cancer, Hepatocellular Carcinoma; High-Grade Childhood Cerebral Astrocytoma; Hypereosinophilic Syndrome; Hypopharyngeal Cancer; Idiopathic Pulmonary Fibrosis; Inflammatory Myofibroblastic Tumor; Inoperable Locally Advanced Squamous Cell Carcinoma of Head and Neck; Insulinoma; Intraductal Breast Carcinoma; Islet Cell Carcinoma; Kidney and Urinary Cancer; L1 Adult Acute Lymphoblastic Leukemia; L2 Adult Acute Lymphoblastic Leukemia; Large Cell Lung Cancer; Laryngeal Cancer; Leukemia, Lymphocytic, Acute L2; Leukemia, Myeloid, Chronic; Leukemia, Myeloid, Chronic Phase; Lip and Oral Cavity Cancer; Lip Cancer; Liver Cancer; Liver Dysfunction and Neoplasm; Localized Unresectable Adult Primary Liver Cancer; Low-Grade Childhood Cerebral Astrocytoma; Lymphoid Blastic Phase of Chronic Myeloid Leukemia; Lung Adenocarcinoma With Bronchiole-Alveolar Feature; Lung Cancer; Male Breast Cancer; Malignant Fibrous Histiocytoma; Malignant Melanoma; Mastocytosis; Medullary Thyroid Cancer; Melanoma; Meningeal Tumors; Meningeal Hemangiopericytoma; Meningioma; Meningioma; Meningioma; Mesothelioma; Metastatic Cancer; Metastatic Solid Tumors; Metastatic Colorectal Cancer; Metastatic Gastrointestinal Carcinoid Tumor; Metastatic Pancreatic Carcinoma; Mixed Gliomas; Multiple Myeloma; Musculoskeletal Tumors; Myelodysplastic Syndrome; Myelogenous Leukemia, Acute; Myelofibrosis; Myeloid Leukemia, Chronic; Myeloid Leukemia, Chronic Accelerated-Phase; Myeloid Leukemia, Chronic, Chronic-Phase; Myeloid Metaplasia; Myeloproliferative Disorder (MPD) with Eosinophilia; Nasopharyngeal Cancer; Nasopharyngeal Carcinoma; Neoplasms; Neuroblastoma; Neurofibrosarcoma; Non-B Childhood Acute Lymphoblastic Leukemia; Non-Metastatic (T2-T4, N0-N3, MO; Stages II and III) and Histologically-Confirmed Intestinal GC; Non-Metastatic Prostate Cancer; Nonresectable Adrenocortical Carcinoma; Non-Small Cell Lung Cancer; Nose Cancer; Oligodendroglioma; Oligodendroglial Tumors; Oral Cancer; Oropharyngeal Cancer; Osteosarcoma; Ovarian Cancer; Ovarian Epithelial Cancer; Ovarian Germ Cell Tumor; Ovarian Low Malignant Potential Tumor; Ovarian Neoplasms; Pancreatic Cancer; Papillary Thyroid Cancer; Pelvic Neoplasms; Peritoneal Cavity Cancer; Peritoneal Carcinoma; Peritoneal Neoplasms; Pharynx Cancer; Philadelphia Chromosome Positive Chronic Myelogenous Leukemia; Philadelphia Positive Acute Lymphoblastic Leukemia; Philadelphia Positive Chronic Myeloid Leukemia in Myeloid Blast Crisis; Pneumonic-Type Adenocarcinoma (P-ADC); Polycythemia Vera; Pulmonary Fibrosis; Primary Hepatocellular Carcinoma; Primary Liver Cancer; Prostate Cancer; Prostate Cancer, Antigen Independent; Rectal Cancer; Recurrent Adult Brain Tumor; Recurrent Adult Soft Tissue Sarcoma; Recurrent Adult Primary Liver Cancer; Recurrent Breast Cancer; Recurrent Cervical Cancer; Recurrent Colon Cancer; Recurrent Endometrial Cancer, Recurrent Esophageal Cancer; Recurrent Gastric Cancer; Recurrent Glioblastoma; Recurrent Glioblastoma Multiforme (GBM); Recurrent Kaposi's Sarcoma; Recurrent Melanoma; Recurrent Merkel Cell Carcinoma; Recurrent Ovarian Epithelial Cancer; Recurrent Pancreatic Cancer; Recurrent Prostate Cancer; Recurrent Rectal Cancer; Recurrent Salivary Gland Cancer; Recurrent Skin Cancer; Recurrent Small Cell Lung Cancer; Recurrent Tumors of the Ewing's Family; Recurrent Uterine Sarcoma; Refractory Germ Cell Tumors Expressing EGRF; Relapsing Chronic Myelogenous Leukemia; Renal Cell Cancer; Renal Cell Carcinoma; Renal Papillary Carcinoma; Rhabdomyosarcomas; Salivary Gland Adenoid Cystic Carcinoma; Sarcoma; Sarcomatous Mesothelioma; Skin Cancer; Small Cell Lung Cancer; Soft Tissue Sarcoma; Squamous Cell Carcinoma; Squamous Cell Carcinoma of the Esophagus; Squamous Cell Carcinoma of the Head and Neck; Squamous Cell Carcinoma of the Skin; Squamous Cell Lung Cancer; Stage II Esophageal Cancer; Stage III Esophageal Cancer, Stage II Melanoma; Stage II Merkel Cell Carcinoma; Stage III Adult Soft Tissue Sarcoma; Stage III Esophageal Cancer; Stage III Merkel Cell Carcinoma; Stage III Ovarian Epithelial Cancer; Stage III Pancreatic Cancer; Stage III Salivary Gland Cancer; Stage IIIB Breast Cancer; Stage IIIC Breast Cancer; Stage IV Adult Soft Tissue Sarcoma; Stage IV Breast Cancer; Stage IV Colon Cancer; Stage IV Esophageal Cancer; Stage IV Gastric Cancer; Stage IV Melanoma; Stage IV Ovarian Epithelial Cancer; Stage IV Prostate Cancer; Stage IV Rectal Cancer; Stage IV Salivary Gland Cancer; Stage IVA Pancreatic Cancer; Stage IVB Pancreatic Cancer; Systemic Mastocytosis; Synovial Sarcoma; T-lymphoma; T-Cell Childhood Acute Lymphoblastic Leukemia; Testicular Cancer; Thorax and Respiratory Cancer; Throat Cancer; Thyroid Cancer; Transitional Cell Cancer of the Renal Pelvis and Ureter; Transitional Cell Carcinoma of the Bladder; Tubal Carcinoma; Unresectable or Metastatic Malignant Gastrointestinal Stromal Tumor (GIST); Unspecified Childhood Solid Tumor; Unspecified Adult Solid Tumor; Untreated Childhood Brain Stem Glioma; Urethral Cancer; Uterine Carcinosarcoma, and Uterine Sarcoma.

Examples

A randomized trial was conducted to evaluate the antitumor activity of fosbretabulin tromethamine (CA4P) in mice bearing subcutaneous EMT-6 mouse mammary tumor cells in combination with other treatments. Other treatments include a combination treatment with anti-CTLA-4 antibody (ref: BE0131, Bioxcell; clone: 9H10; reactivity: mouse; isotype: Hamster IgG1; storage conditions: +4° C.).

CA4P and anti-CTLA-4 antibodies were prepared in phosphate buffered saline (PBS). CA4P was injected at the dose of 100 mg/kg. The anti-CTLA-4 antibody was injected at the dose of 10 mg/kg. The tested items were injected into the peritoneal cavity of mice (e.g. intraperitoneally, IP). The administration volume was 10 mL/kg (200 µL/mouse of 20 g) adjusted to the most recent individual body weight of the mice.

An EMT-6 cell line having an ATCC origin and a culture medium was used. The EMT-6 cell line was established from a transplantable murine mammary carcinoma that arose in a BALB/cCRGL mouse after implantation of a hyperplastic mammary alveolar nodule. EMT-6 tumor cells were grown as a monolayer at 37° C. in a humidified atmosphere (5% $CO_2$, 95% air). The culture medium was RPMI 1640 containing 2 mM L-glutamine (ref: BE12-702F, Lonza, Verviers, Belgium) supplemented with 10% fetal bovine serum (ref: 3302, Lonza).

Healthy female Balb/C mice, 6-8 weeks old at reception, were used in the study. The treatment started when the tumors reached a mean volume of approximately 75-150 mm$^3$. The mice were randomized according to their individual tumor volume into groups of 8 animals each using Vivo Manager® software (Biosystemes, Couternon, France). A statistical test (analysis of variance) were performed to test for homogeneity between groups. The treatment schedule was as follows:

| Group | No. Animals | Treatment | Dose (mg/kg/inj) | Route | Treatment Schedule |
|---|---|---|---|---|---|
| 1 | 8 | Vehicle | — | IP | TWx2 |
| 2 | 8 | CA4P | 100 | IP | TWx2 |
| 3 | 8 | Anti-CTLA-4 | 10 | IP | TWx2 |
| 4 | 8 | CA4P | 100 | IP | TWx2 |
|   |   | Anti-CTLA-4 | 10 | IP | TWx2 |

TWx2 refers to one injection twice weekly for two consecutive weeks. CA4P were administered 24 hours prior to each dose of the antibody.

Figure 1:
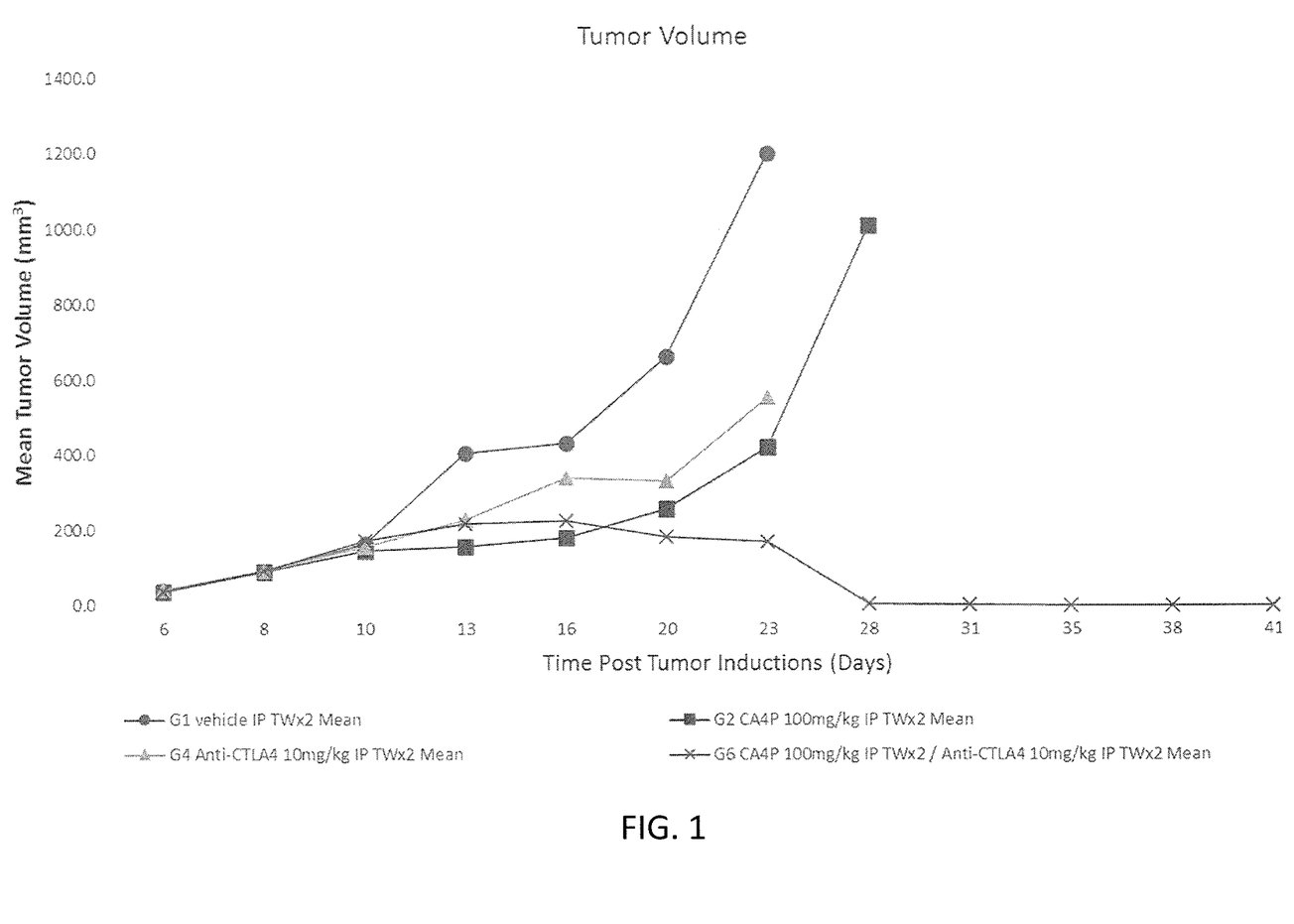
FIG. 1 is a graph illustrating tumor volume versus time post tumor induction for mice in a study.
Figure 2:
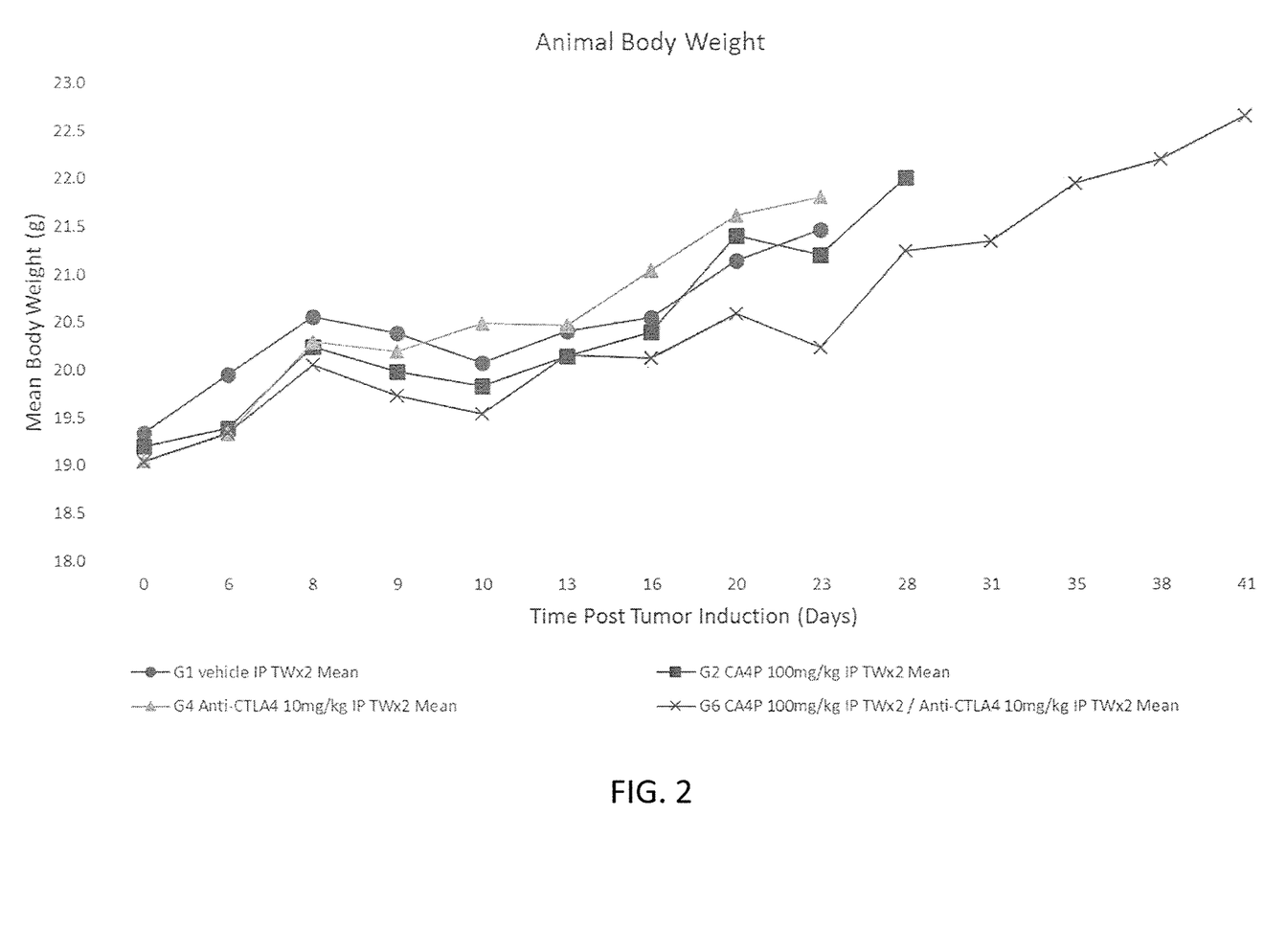
FIG. 2 is a graph illustrating body weight versus time post tumor induction for mice in a study.

Results for the tumor volume versus time and the body weight versus time for the mice in the study are illustrated in FIGS. 1-2, respectively. Once more than 20% of the mice were dead in a given group then the study was discontinued for the given group. FIG. 1 shows that the average tumor size decreased significantly for the mice that received both CA4P and anti-CTLA-4 in contrast to the control group, CA4P only group, and the anti-CTLA-4 only groups where tumor sizes steadily increased on average. Two of the eight mice receiving anti-CTLA-4 only showed tumor regression with the treatment. One of the eight mice receiving CA4P only showed tumor regression. Unexpectedly, seven of the eight mice receiving both CA4P and anti-CTLA-4 showed complete tumor regression. Seven of the eight mice receiving both CA4P and anti-CTLA-4 were still alive at the 41 day mark of the study. The combination treatment with both CA4P and anti-CTLA-4 resulted in a synergistic effect against the tumors in the mice exemplified by the increased/complete tumor regression, increased survival rate, and significantly extended lifespan of the mice treated with both CA4P and anti-CTLA-4 in the study.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A pharmaceutical composition for producing an anti-tumor effect in a subject suffering from cancer or a tumor, comprising a Vascular Disrupting Agent (VDA) comprising a combretastatin agent and one or more antibodies selected from the group consisting of: a CTLA-4 antibody, a PD-1 antibody, a PD-L1 antibody, and a PD-L2 antibody in amounts effective therefore in a pharmaceutical carrier, where in the VDA is combretastatin A1 diphosphate (CA1P) or combretastatin A4 phosphate (CA4P), or a compound of formula III shown:

wherein the wherein OR', OR2, OR and OR4 are each, independently, H, —O— QH+ or —O— M+, wherein M+ is a monovalent or divalent metal cation, and Q is, independently:
a) an amino acid containing at least two nitrogen atoms where one of the nitrogen atoms, together with a proton, forms a quaternary ammonium cation QH+; or
b) an organic containing at least one nitrogen atom which, together with a proton, forms a quaternary ammonium cation, QH+ and pharmaceutically acceptable salts thereof.

2. The composition of claim 1, wherein the CTLA-4 antibody, PD-1 antibody, PD-L1 antibody, and a PD-L2 antibody are selected from the group consisting of: Tremelimumab, Ipilumab, Nivolumab, Pembrolizumab, Pidilizumab, MEDI4736, BMS 936559, MPDL328OA, and AMP-224.

3. The composition of claim 1, wherein the VDA is combretastatin A1 diphosphate (CA1P) or combretastatin A4 phosphate (CA4P).

4. The composition of claim 1, said pharmaceutical composition comprising CA1P and one or more compounds selected from the group consisting of: Tremelimumab, Ipilumab, Nivolumab, Pembrolizumab, Pidilizumab, MEDI4736, BMS 936559, MPDL328OA, and AMP-224.

5. The composition of any claim 1, said pharmaceutical composition comprising CA4P and one or more compounds selected from the group consisting of: Tremelimumab, Ipilumab, Nivolumab, Pembrolizumab, Pidilizumab, MEDI4736, BMS 936559, MPDL328OA, and AMP-224.

* * * * *